United States Patent [19]

Kelen

[11] 4,291,703
[45] Sep. 29, 1981

[54] PACEMAKER MONITORING RECORDER

[75] Inventor: George J. Kelen, Staten Island, N.Y.

[73] Assignee: Del Mar Avionics, Irvine, Calif.

[21] Appl. No.: 106,692

[22] Filed: Dec. 26, 1979

Related U.S. Application Data

[62] Division of Ser. No. 956,878, Nov. 1, 1978, abandoned.

[51] Int. Cl.³ ............................................. A61B 5/04
[52] U.S. Cl. ............................ 128/711; 128/419 PT
[58] Field of Search ................. 128/697, 711, 419 PT

[56] References Cited

U.S. PATENT DOCUMENTS

| | | | |
|---|---|---|---|
| 3,651,280 | 3/1972 | Streckmann | 128/711 |
| 3,872,252 | 3/1975 | Malchman et al. | 128/697 |
| 3,923,041 | 12/1975 | Stasz et al. | 128/697 |

*Primary Examiner*—William E. Kamm
*Attorney, Agent, or Firm*—Smyth, Pavitt, Siegemund & Martella

[57] ABSTRACT

A recorder for monitoring the operation of a cardiac pacemaker and the response of the patient to the pacemaker includes a recorder module which receives a composite signal including an ECG signal, a pacemaker spike having a frequency spectrum that lies substantially at frequencies greater than the frequency band required to pass the ECG signal, and further includes artifact noise within the frequency spectrum of the pacemaker spike. The recorder module distinguishes the pacemaker spike from the artifact noise and upon recognizing the pacemaker spike, the recorder module produces a distinctive synthesized signal whose frequency spectrum lies substantially within the frequency band required to pass the ECG signal so that the synthesized signal will pass through the pre-emphasis filter that is used to reject artifact noise and will then be recorded.

5 Claims, 7 Drawing Figures

Fig. 6

PACEMAKER MONITORING RECORDER

CROSS REFERENCE TO RELATED APPLICATION

This application is a divisional of U.S. application Ser. No. 956,878, filed Nov. 1, 1978, now abandoned, entitled PACEMAKER MONITORING RECORDER AND MALFUNCTION ANALYZER.

BACKGROUND OF THE INVENTION

1. Field of the Invention

The present invention is in the field of electrocardiography and more specifically relates to a system for the ambulatory monitoring of pacemaker operation.

2. Prior Art

The present invention is another step forward in the continuing development of instrumentation for ambulatory (Holter) monitoring. Such techniques are more widely used each year owing to a growing appreciation of the diagnostic value of measurements made while the patient pursues his daily activities. Typically, the measurements are recorded on a portable tape recorder affixed to the patient. The recorded tape may subsequently be scanned, analyzed, and plotted. A 24-hour recording can be scanned and analyzed in less than half an hour, and sporadic pauses, trachycardia or bradycardia, and premature contractions can be detected with confidence. It is also possible to detect and to count premature beats, either ventricular or supraventricular.

An early example of a system for recording and playing back ECG signals is found in U.S. Pat. No. 3,215,136, issued Nov. 2, 1965 to Holter, et al. The present state of the art is represented by the device disclosed in U.S. Pat. No. 4,006,737, issued Feb. 8, 1977, to Cherry and in U.S. Pat. No. 4,073,011, issued Feb. 7, 1978, to Cherry and Anderson for "Electrocardiographic Computer". A reissue application of the latter patent was filed Apr. 24, 1978, and a divisional application Ser. No. 773,618, filed Mar. 2, 1977, is directed to a recorder for cardiac signals. A much improved recorder is described in application Ser. No. 918,698 filed June 23, 1978, for "Recorder for Ambulatory Monitoring of Electrocardial Signals" by Shu and Squires.

At the same time that the aforementioned ambulatory monitoring techniques were being developed, other technologists were working to make practical the use of artificial pacemakers, implanted in patients to stabilize their heart rates. Pacemakers are now routinely implanted and there are presently more than 50,000 people in the United States dependent on implanted pacemakers.

Artificial pacemakers supply an electrical stimulation to the heart when it tends to beat irregularly due to a partial or complete block in the heart's conduction system. There are two main types of pacemakers: the fixed rate pacemaker and the demand pacemaker. As the names indicate, the fixed rate pacemaker attempts to pace the heart 100% of the time at a fixed frequency. It soon was recognized that the fixed rate pacemaker was not desirable in those situations in which a partial block of the heart's conduction system left the heart capable of spontaneously beating for appreciable times. In this situation, competition between the fixed rate pacemaker and the remaining spontaneous heart action led to problems. It was this situation which led to the development of the demand pacemaker. The demand pacemaker senses the heart's spontaneous action and operates only when the spontaneous action is inadequate.

Although the reliability of pacemakers is generally excellent, three major types of pacemaker failure have been documented: lead or electrode failure, circuit failure, and battery exhaustion, the latter being by far the most frequent. These types of failure may manifest themselves in any of several observable types of abnormal pacemaker operation. One manifestation is abnormal bradycardia, wherein the time interval between successive spontaneous heart beats is longer than the pacemaker should permit without intervention. That is, the pacemaker fails to apply a stimulative pulse even though the spontaneous beats of the heart are excessively slow.

Somewhat the opposite of abnormal bradycardia is the manifestation of pacemaker failure known as failure-to-sense. In this mode, a spontaneous heart beat is followed prematurely by a pacemaker spike. That is, the pacemaker spike occurs sooner after the spontaneous beat than it should if the pacemaker were functioning properly. This type of failure appears to indicate that the pacemaker failed to sense the spontaneous heartbeat and went ahead to produce a stimulative spike in spite of the spontaneous operation of the heart.

Another manifestation of pacemaker failure is the observed failure-to-capture. This defective mode of operation results when a pacing spike fails to be followed within 30 milliseconds by the onset of a heartbeat. This mode of failure appears to indicate that the spike generated by the pacemaker was inadequate to trigger a heartbeat.

In contrast to the aforementioned three manifestations of pacemaker failure is the normal mode of operation, wherein a pacemaker spike is followed by the onset of a hearbeat within five to forty milliseconds later. Like the paced beat, the fusion beat is also considered to be normal. A fusion beat results when a pacemaker impulse is followed within five milliseconds by the onset of a heartbeat. This indicates that the heart is spontaneously beating at approximately the frequency called for by the pacemaker.

Failure-to-sense, failure-to-capture, and abnormal bradycardia may occur intermittently making detection and confirmation of pacemaker malfunction difficult, in accordance with Murphy's Law. Clearly, the detection and confirmation of intermittent pacemaker malfunction would be greatly facilitated if the operation of the pacemaker were monitored over an extended time period, and under a wide range of patient activities. For this reason, Holter monitoring of pacemaker operation would appear to offer the ideal solution.

However, when one records and scans a tape from a patient with an artificial pacemaker, a number of frustrating difficulties arise if there is alternation between paced and spontaneous beats. It may indeed be difficult or impossible to detect intermittent pacemaker malfunction unless it causes a significant disturbance of heart rate.

There are two principal reasons for this. First, in commercially available Holter monitoring equipment, the frequency response of the recording playback system is usually intentionally tailored by the manufacturer to minimize false signals introduced by muscular contractions and other artifacts. As a result of the attenuation of this specially shaped frequency response, the pacemaker spikes tend to be slurred and greatly reduced in amplitude, making it often impossible to distinguish on the basis of structure a paced beat from a premature ventricular contraction or other wide but spontaneous QRS complex.

The second major problem encountered in attempting to detect intermittent pacemaker malfunction on conventional ambulatory monitoring equipment is that the features of pacemaker sensing failure or capture failure are simply not visible on the display of the playback unit when the recorded tape is played back at higher scanning speeds, such as ×30 to ×120. Even those scanners which have the ability to count premature ventricular contractions are not able to recognize the pacemaker related events.

Thus, there is a need in the art for a system to permit ambulatory monitoring of pacemaker operation over time periods measured in hours, and to permit rapid scanning and analysis of the recorded data so as to recognize the occurence of intermittent pacemaker malfunction.

SUMMARY OF THE INVENTION

The present invention fills the need for a system which will permit the ambulatory recording of both spontaneous heartbeats as well as pacemaker-generated pulses and which permits the various manifestations of pacemaker malfunction to be recognized when the recorded tape is played back at high speed. In one embodiment of the present invention, when a pacemaker malfunction is recognized during the high speed playback, the tape is slowed to real time speed to permit plotting of the pertinent portion of the data for detailed analysis.

Two-channel recorders for use in ambulatory monitoring of patients without artificial pacemakers are described in U.S. patent application Ser. No. 773,618 filed Mar. 2, 1977 by Cherry and Anderson for "Recorder For Cardiac Signals" and in U.S. patent application Ser. No. 918,698 filed June 23, 1978 by Shu and Squires for "Apparatus For Recording and Playing Back Electrocardial Signals". Apparatus used for playing back and analyzing the tape recorded from a patient without a pacemaker is described in U.S. Pat. No. Re 29,921 issued to Cherry et al. for Electrcardiographic Computer. All of the applications and patents referred to above are assigned to the assignee of the present invention.

Once the tape has been recorded on the equipment described in the references cited above, the tape is played back at 120 times the speed at which it was recorded, thus taking twelve minutes to scan a 24-hour recording. At these speeds, heavy reliance is placed on computerized initial detection of abnormalities. Subsequent detailed analysis of a section of tape recognized as including abnormalities is usually done with the tape running at real time speed.

In one embodiment of the present invention a spike detecting module is used in conjunction with a commercial two-channel Holter recorder, and no internal modifications to the recorder are necessary. The spike detecting module is a small battery-operated device worn by the patient during the monitoring session. The spike detecting module is connected between the three conventional electrodes applied to the patient's skin and the channel 2 input of the recorder. The function of the spike detecting module is to detect a pacemaker spike whenever one occurs, and thereupon to generate a square wave pulse large enough and wide enough to pass the tape recorder's pre-emphasis filter. Channel 1 of the recorder is connected in conventional fashion and records the spontaneous beats in the normal manner. The pacemaker discharge is always indicated by a pulse of predetermined shape on Channel 2 of the recording. The initial deflection of this pulse coincides with occurence of an artificial pacemaker discharge. The time-correlated signal recorded on Channel 1 consists of a series of QRS complexes in a normal patient.

The spike detecting module is small and light in weight, so that it imposes no appreciable additional burden on the ambulatory patient. The current consumption of the spike detecting module is very low. Significantly, the spike detecting module is reliably triggered by pacemaker spikes of varying amplitudes and rise times, and is substantially immune to triggering by other stimuli including QRS complexes and muscle artifacts.

In a preferred embodiment, the output of the spike detecting module is a square pulse of amplitude between two and four millivolts and having duration sufficient to pass easily through the pre-emphasis filter at the input of the recorder; i.e., the pulse duration is approximately 40 milliseconds in a preferred embodiment. The spike detecting module has low output impedance so as to minimize hum pick up and to be compatible with the input circuit of the recorder. With separate clear indications of pacemaker spikes and QRS complexes on the two channels respectively, it becomes possible to recognize various manifestations of pacemaker failure.

For example, failure-to-capture occurs when a pacing spike on channel 2 is not followed by a QRS complex on channel 1 within a predetermined interval, such as approximately forty milliseconds of real time. Likewise, failure of the pacemaker to sense the occurence of a spontaneous beat is recognized when a pacing spike on channel 2 prematurely follows a spontaneous QRS complex on channel 1. Similarly, failure of the pacemaker to produce an effective pulse is indicated by an abnormally long R—R interval (abnormal bradycardia) on channel 1 accompanied by an absence of intervening pacemaker spikes in channel 2.

In addition to these manifestations of pacemaker failure, it is possible to recognize when the pacemaker is operating normally. Thus, a normal paced beat is recognized when a pacing spike on channel 2 is followed within 40 milliseconds by a QRS complex on channel 1. If the pacing spike coincides with the spontaneous initiation of a QRS complex the occurence of a fusion beat is recognized.

In a preferred embodiment of the present invention, these criteria for the recognition of fusion beats, paced beats, abnormal bradycardia, failure to capture and failure to sense are implemented in a module which receives the channel 1 (ECG) and channel 2 (pacemaker) signals from the playback apparatus and monitors the time relationship between the pacemaker spikes and the ECG complexes as the tape is played back at high speed. The module includes circuitry which establishes time gates in accordance with the criteria that define the various events to be recognized, and further includes logic circuits for recognizing the occurrence of each type of event, and counters for displaying the accumulated number of paced beats and fusion beats. In a preferred embodiment, when the module detects failure-to-sense, failure-to-capture, or abnormal bradycardia, it generates a signal which is applied to the playback unit to cause the playback unit to revert temporarily to a slower speed to facilitate manual observation, analysis, and mechanized plotting of the signals.

The system of the present invention makes practical the application of ambulatory (Holter) monitoring of pacemaker operation for the rapid and reliable detection of pacemaker malfunction. Surveillance of hours of pacemaker operation can be scanned and analyzed in a matter of minutes. For this reason, the apparatus of the present invention is very well suited for the screening of symptomatic patients with pacemakers. Such screening permits both routine periodic follow-up evaluation of pacemaker performance and prediction of pacemaker power source longevity based upon the determined frequency of the pacemaker discharge.

The novel features which characterize the invention both as to its structure and method of operation, together with further objects and advantages thereof, will be better understood from the following description considered in connection with the accompanying drawings in which a preferred embodiment of the invention is illustrated by way of example. It is to be expressly understood, however, that the drawings are for the purpose of illustration and description and are not intended as a definition of the limits of the invention.

DESCRIPTION OF THE PREFERRED EMBODIMENT

Figure 1:
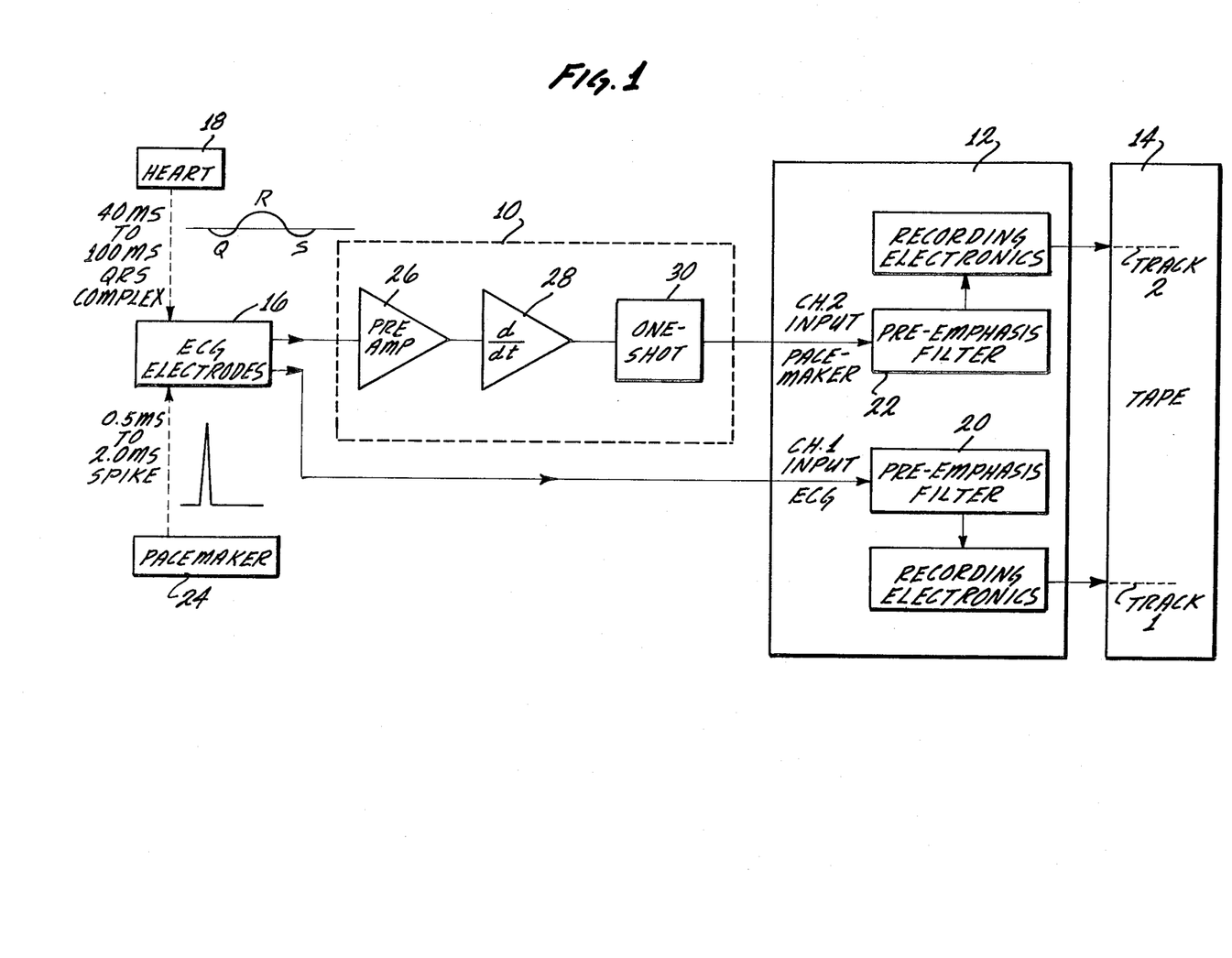
FIG. 1 is a circuit diagram of the pacemaker spike sensing and recording module.

Turning to the drawings in which like parts are denoted by the same reference numeral, there is shown in FIG. 1 a recorder module 10 for use with a recorder 12 to permit both ECG signals and pacemaker spikes to be recorded on a magnetic tape 14.

Electrical signals from the heart 18 are senses by the ECG electrodes 16 and are applied to the channel 1 input of the recorder 12.

Most of the frequency components of the ECG signal are at low frequencies, and a bandpass of 0-100 Hz is adequate for most purposes. Advantage is taken of the known spectrum of the ECG signal to filter out artifact noises. Normally, the recorder 12 includes a pre-emphasis filter 20 which permits the ECG signals to pass through the recorder to be recorded, but which effectively eliminates the artifact noise.

As indicated in FIG. 1, the width of the pacemaker spike is much less than the width of the QRS complex found in the ECG signal. Accordingly, most of the power of the pacemaker spike signal is concentrated in a higher frequency range than the bandpass of the pre-emphasis filter 20, and thus the pacemaker spike signal would be severely distorted and attenuated by the pre-emphasis filter of the recorder.

In a preferred embodiment of the present invention, electrical signals from the implanted pacemaker 24 are picked up by the ECG electrodes 16 and applied to the recorder module 10 which produces a recordable signal and applies it to the Channel 2 input of the recorder. In the preferred embodiment, the pacemaker spike signals and the ECG signals are recorded on separate tracks on the magnetic tape 14. The recorder module 10 permits the time of occurrence of the pacemaker spike to be determined very accurately when the tape 14 is played back.

The recorder module 10 includes a pre-amplification stage 26 followed by a differentiator 28 followed by a one-shot multivibrator 30. The pacemaker spike is generally of much greater amplitude than the artifact noise, and the leading edge of the pacemaker spike is much more steep than the normal QRS complexes which, along with the artifact noise, are also present at the input to the amplifier 26. The present invention takes full advantage of the steep leading edge of the pacemaker spike by use of the differentiator 28. Of the signals coming out of the differentiator 28, those derived from the pacemaker spike signal have by far the greatest amplitude. The one-shot 30 includes a threshold which is set at such a level that only the signals derived from pacemaker spikes are able to trigger the one-shot 30, which when triggered, produces a pulse having a duration of at least 10 milliseconds, typically. Because the frequency components of the pulse produced by the one-shot 30 are mainly at the low frequencies, comparable to the frequencies of the QRS complexes, the pulses pass readily through the pre-emphasis filter 22 and are recorded on track 2 of the tape 14.

It should be noted that the recorder module 10 does more than merely precondition the shape of the pacemaker spike pulses; it also substantially eliminates ECG signals and artifact noise from Channel 2. This achieves a separation of the pacemaker spike pulses and the ECG signals permitting them to be recorded on separate time-correlated tracks on the tape, even though the single set of ECG electrodes 16 pick up a composite signal including the QRS complexes, the pacemaker spikes, and the artifact noise.

The speed of the tape 14 at the time the signals are recorded on it is called the real time speed. During playback, the tape is normally moved at a higher speed.

Figure 2:
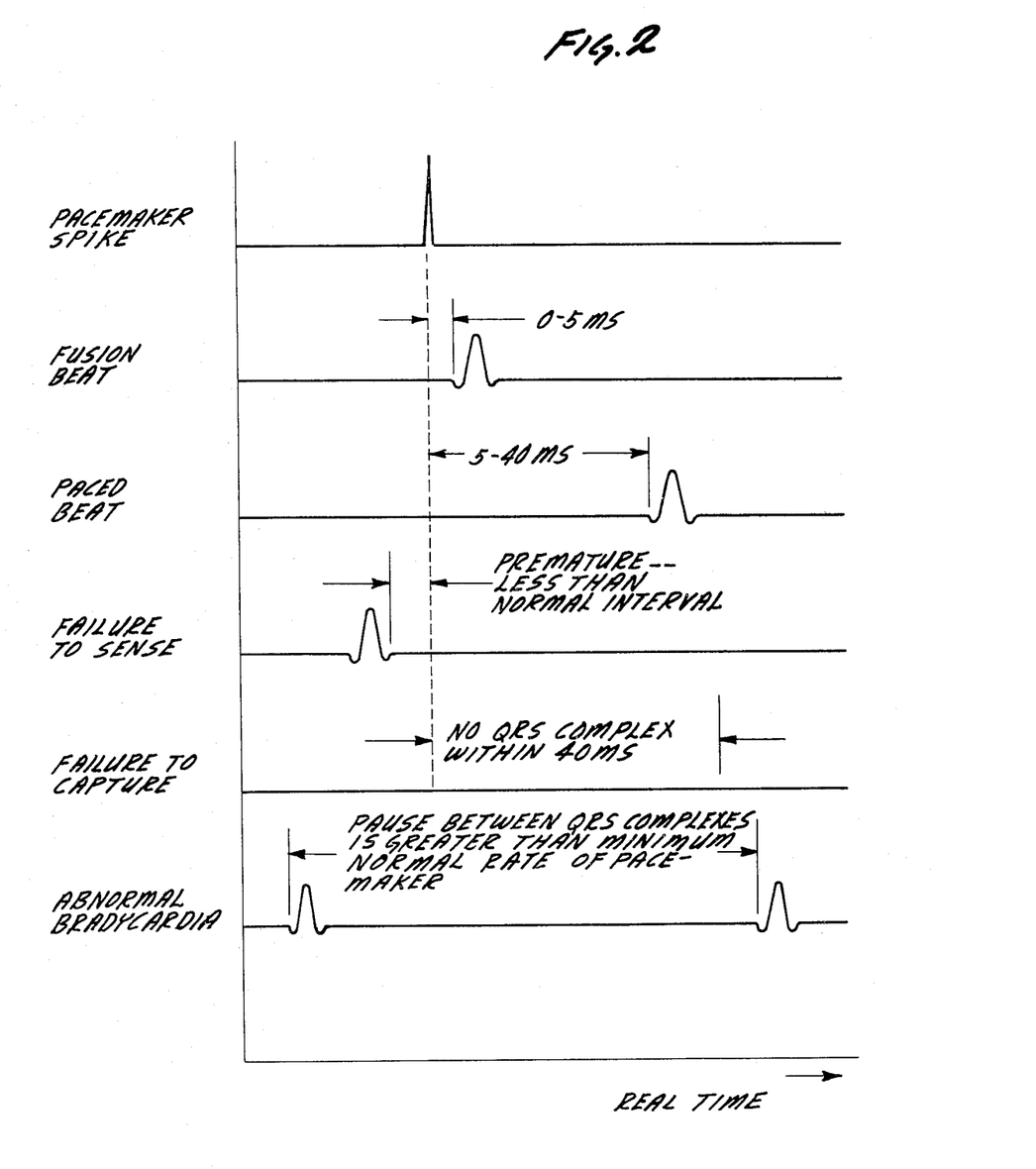
FIG. 2 is a timing diagram showing the criteria used in defining the various events whose occurrence is recognized by the analyzer mocule.

FIG. 2 is a graph showing a number of wave forms, and is useful for defining the terms listed along the left side of the figure, as those terms are used in the present description. A paced beat is an ECG signature stimulated by the pacemaker spike and occurring between 5 and 40 milliseconds after the pacemaker spike. If the heart is beating spontaneously and approximately in synchronism with the pacemaker, it is possible that a fusion beat will approximately coincide with the pacemaker spike, but will actually follow the pacemaker spike by 0 to 5 milliseconds. If the spontaneous and approximately synchronized beat had occurred before the pacemaker spike, its occurrence would have been sensed by a pacemaker of the demand type and the pacemaker spike would have been suppressed. If, however, the pacemaker spike is not suppressed, the pacemaker is deemed to have failed to sense the heart beat.

If no QRS complex occurs within 40 milliseconds of the occurrence of the pacemaker spike, the pacemaker is said to have failed to capture the operation of the heart, which in spite of the generation of a pacemaker spike does not respond in the normal time.

If successive QRS complexes occur at a rate which is slower than the normal minimum rate of the pacemaker, there is deemed to be an abnormal bradycardia.

Paced beats and fusion beats are normal phenomena and do not indicate any malfunction of the pacemaker. However, failure-to-sense, failure-to-capture, and abnormal bradycardia are manifestations of pacemaker malfunction. It is useful to know the relative numbers of fusion beats and paced beats which occur in a given time interval.

In a preferred embodiment, the apparatus shown in FIG. 1 is normally affixed to the patient so that the operation of his heart and of the pacemaker can be monitored while the patient moves about. The recorder 12 has sufficient capacity to permit recording sessions as long as 24 hours. Typically, abnormal operation may be manifest for short intervals during the recording session. If the magnetic tape were played back at real time speed, it would be necessary for an analyst to observe a display of the played-back signals for the full 24 hour duration. To avoid this time-consuming and expensive use of the analyst's time, the tape is normally played back at 60 or 120 times the real time speed. In the following description, the numerical values given will be applicable to the ×120 playback speed, although the appropriate values for use at the ×60 speed can easily be determined from the disclosure herein.

Figure 3:
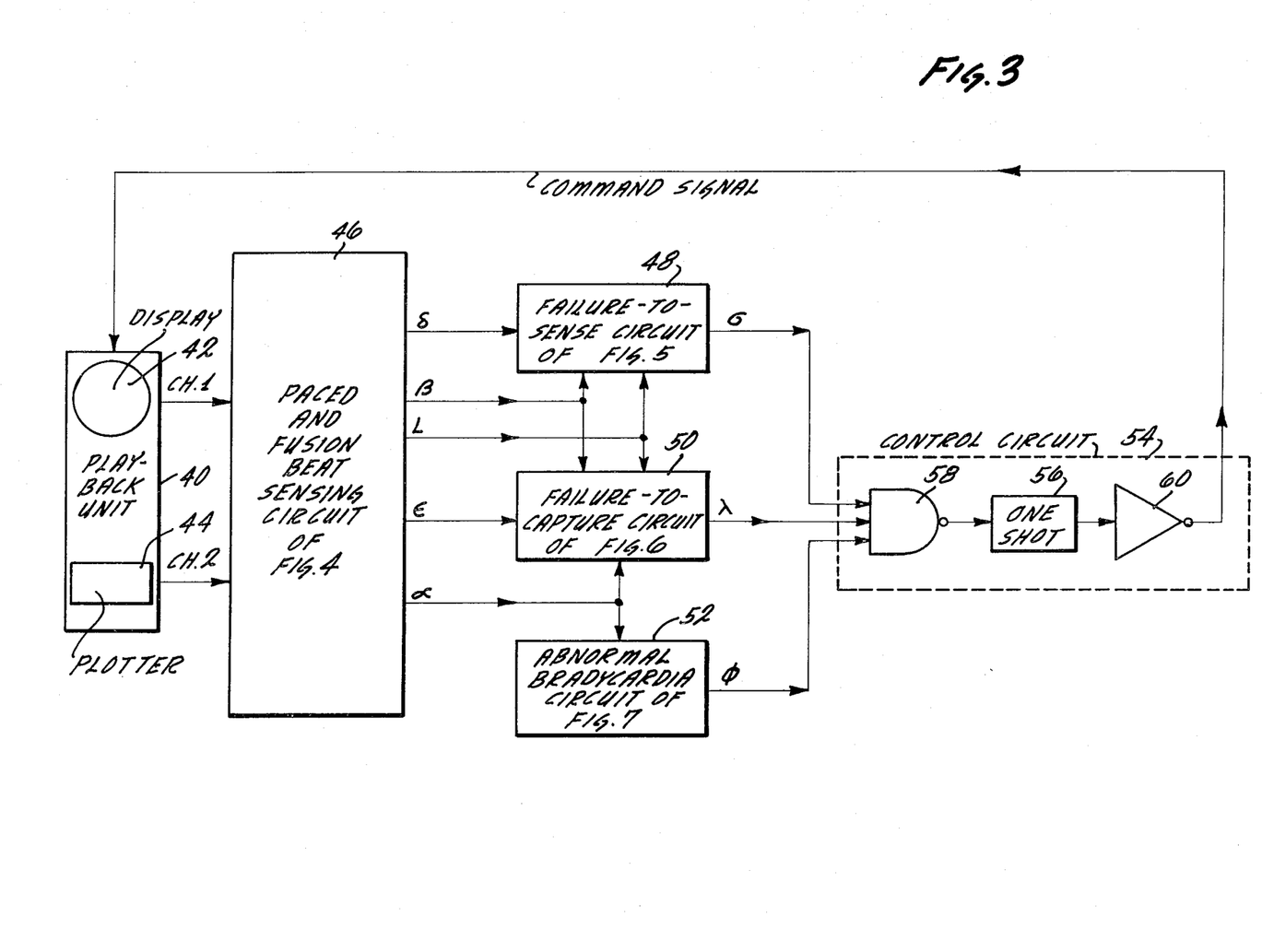
FIG. 3 is a block diagram of the analyzer module shown connected to the playback unit.

FIG. 3 is a block diagram of the system used in a preferred embodiment for playing back and analyzing the recorded tape. The system shown in FIG. 3 includes the playback unit 40 and the remainder of the circuit shown in FIG. 3 is an analysis module for use with the playback unit. The recorded tape is inserted into the playback unit 40 which includes a display 42 and a plotter 44 to permit visualization of the recorded signals. The ECG and pacemaker signals are presented as the channel 1 and channel 2 outputs, respectively, of the playback unit to the paced and fusion beat sensing circuit 46. The paced and fusion beat sensing circuit 46 includes counters for counting the numbers of paced and fusion beats that occur in a given time interval. Further, the paced and fusion beat sensing circuit 46 also produces a number of output signals for use in other parts of the analysis module. For example, the signals delta, beta and L are supplied to the failure-to-sense circuit 48; the signals beta, L, and epsilon are supplied to the failure-to-capture circuit 50 along with the alpha signal which is also supplied to the abnormal bradycardia circuit 52.

The failure-to-sense circuit 48 produces a signal, sigma, when the circuit 48 recognizes that the pacemaker has failed to sense. The failure-to-sense circuit 48 also includes an indicator lamp which is activated upon recognizing failure to sense.

The failure-to-capture circuit 50 produces an output signal, lambda, when the circuit 50 recognizes that the pacemaker has failed to capture. The failure-to-capture circuit 50 also includes an indicator lamp which is activated when a failure-to-capture has been recognized.

The abnormal bradycardia circuit 52 produces an output signal, phi, when the circuit 52 recognizes the existence of an abnormal bradycardia condition. The abnormal bradycardia circuit 52 also includes an indicator lamp which is activated upon recognition of the abnormal bradycardia. In the preferred embodiment, the outputs of the circuits 48, 50, 52 are expressed in negative logic so that the failure conditions are indicated by a transition from high to low level. Accordingly, in the preferred embodiment, a NAND gate 58 is used to function as an OR gate to detect the presence of any of the three failure modes. When any of the failure modes is indicated, the one-shot multivibrator 56 produces a pulse which, after inversion by the inverter 60, is applied to the playback unit 40 to cause the playback unit 40 to reduce its speed from, for example, ×120 to real time speed. The NAND gate 58, the one-shot 56, and the inverter 60 make up the control circuit 54. As indicated in FIG. 3, the components of the analysis module are shown in greater detail in FIGS. 4-7. The circuits shown in FIGS. 4-7 are usable over a wide range of playback speeds provided the pulse widths are chosen in relation to the playback speed. The particular values shown for the pulse widths in FIGS. 4-7 are intended for use at the ×120 speed which is exemplary. As is seen from FIG. 3, the ECG and pacemaker output signals of the playback unit 40 are applied to the channel 1 and channel 2 inputs of the paced and fusion beat sensing circuit 46 shown in greater detail in FIG. 4.

Figure 4:
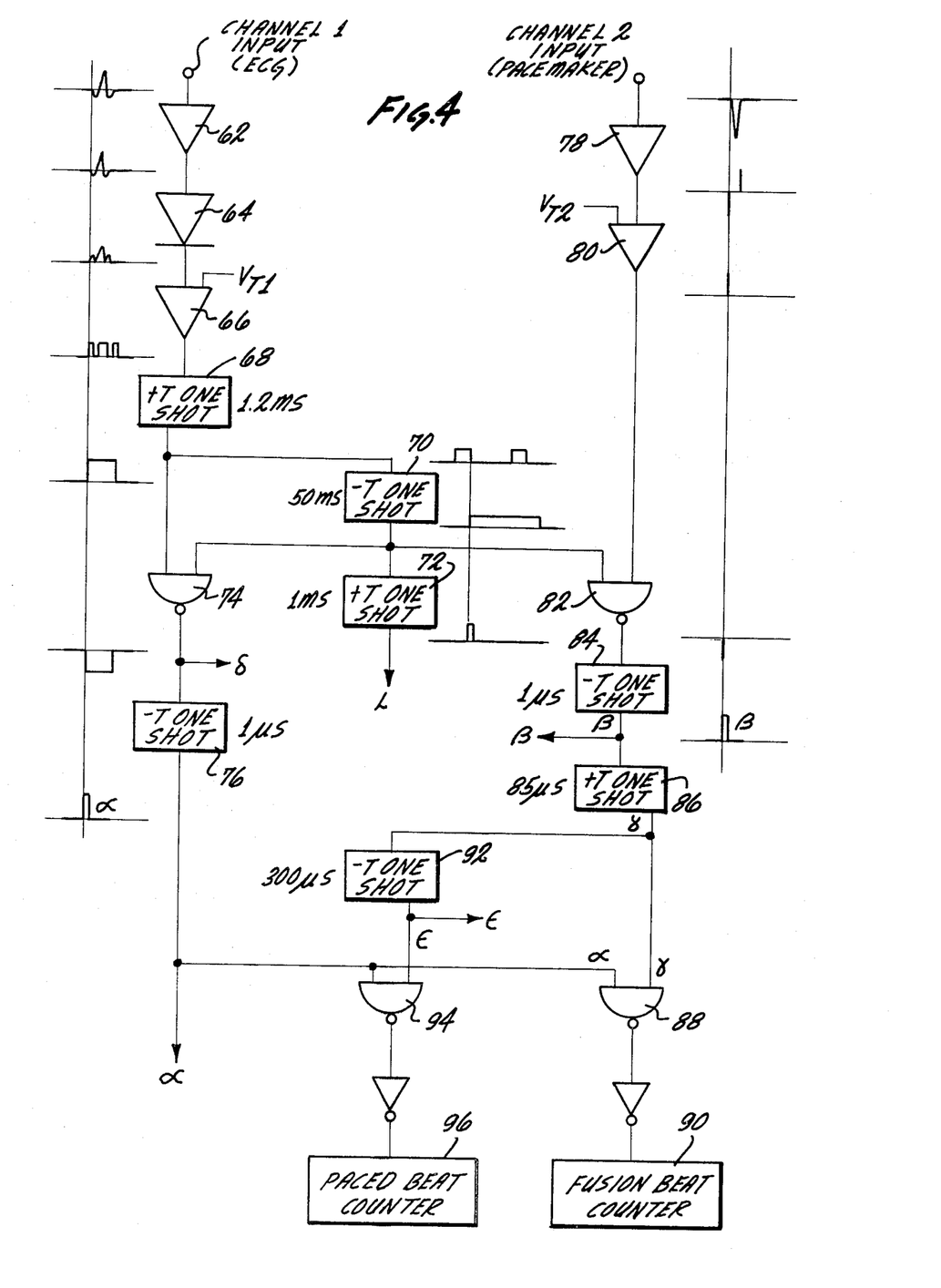
FIG. 4 is a circuit diagram of the paced and fusion beat counter circuit.

As shown in FIG. 4, the reproduced ECG signal is first passed through a 3.3 Khz band pass filter 62. The filter 62 is helpful in attenuating whatever remnants of the pacemaker spike signal and of the artifact noise which might be present in the reproduced ECG channel. Next, the filtered ECG signal is applied to the precision rectifier 64 and then is applied to the comparator 66 which produces a signal suitable for application to the one-shot 68 which, in turn, produces a square pulse whose duration is approximately the same as the duration of the QRS complex. In the drawings, "+T" indicates that the one-shot is triggered by a positive-going transition, and the notation "−T" indicates that the one-shot is triggered on a negative-going transition. In a preferred embodiment, the pulse produced by the one-shot 68 has a duration of approximately 1.2 milliseconds.

The purpose of the retriggerable one-shot 70 and the NAND gates 74, 82 is to prevent spurious generation of the alpha or beta signals when the playback unit switches to ×120 speed at the beginning of each rapid scanning sequence. The gates 74, 82 are disabled until the end of the first QRS complex in a scanning sequence, when the output of one-shot 70 goes positive. The pulse produced by the one-shot 70 is considerably longer than the interval between successive QRS complexes, for example, 50 milliseconds. The positive-going output of the one-shot 70 at the beginning of each rapid scanning sequence is also used to derive through the use of the one-shot 72 a reset pulse for the flip flops shown in FIGS. 5 and 6 (the signal L).

Normally, the output, delta, of the NAND gate 74 is merely the inversion of the output of the one-shot 68. The leading edge of the delta signal is used to trigger the one-shot 76 which produces a narrow pulse, typically one microsecond in length, which serves to mark precisely the beginning of the QRS complex (the signal alpha).

A similar pulse, beta, is generated by the branch at the right side of FIG. 4 to mark the beginning of the pacemaker spike. The pacemaker spike signals from channel 2 of the playback unit 40 are applied to the input of the differentiator 78. The output of the differentiator 78 is passed through the comparator 80 which passes only the pulse corresponding to the leading edge of the pacemaker spike, inverting it. This pulse is applied through the NAND gate 82 to trigger the one-shot 84 to produce the narrow pulse, beta, which typically has a pulse width of 1 microsecond, and which is used to indicate the beginning of the pacemaker spike.

By use of the one-shot 86, triggered by the signal beta, a pulse, gamma, of duration 85 microseconds, is generated. 85 microseconds at ×120 speed is equivalent to 5 milliseconds at real time speed. The signal alpha, which marked the beginning of a QRS complex, and the signal gamma, are applied as inputs to the NAND gate 88 which is used to sense whether a fusion beat has occurred. The simultaneous presence of the alpha and gamma signals indicates the start of a QRS complex within 5 milliseconds following a pacemaker spike, and hence a fusion beat is indicated. The output of the NAND gate 88 is inverted and used to increment the fusion beat counter 90.

A similar arrangement is used for the sensing of paced beats. The one-shot 92 is triggered by the negative-going transition marking the end of the gamma pulse to produce the epsilon pulse typically having a duration of 300 microseconds, which corresponds to 35 milliseconds of real time. The simultaneous occurrence of an alpha pulse, marking the beginning of a QRS complex and an epsilon pulse is sensed by the NAND gate 94 and indicates the occurrence of a paced beat. The output of the NAND gate 94 is inverted and used to increment the paced beat counter 96.

By accumulating the number of paced beats and fusion beats which occur within a given time interval, the circuit of FIG. 4 produces a highly desirable result because it permits the relative numbers of paced and fusion beats to be determined during an ambulatory monitoring session. However, the present invention goes beyond this useful result, and includes the circuitry of FIGS. 5, 6 and 7 for the purpose of recognizing some of the more commonly-occurring manifestations of pacemaker malfunction.

Figure 5:
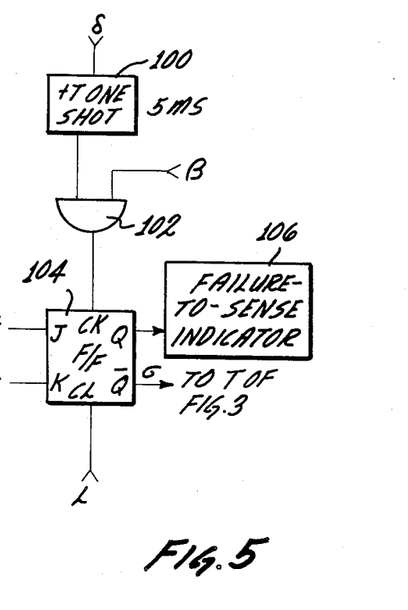
FIG. 5 is a circuit diagram of the failure-to-sense circuit.

The positive-going trailing edge of the signal delta shown in FIG. 4 is used to trigger the one-shot 100 which typically produces a 5 millisecond output pulse. The occurrence of a beta pulse within the 5 millisecond duration of the output of the one-shot 100 indicates the occurrence of a failure-to-sense. This is implemented as shown in FIG. 5 by applying the output of the one-shot 100 and the beta signal as inputs to the AND gate 102. The AND gate 102 senses the failure-to-sense and emits a pulse which is applied to the "clock" input of the flip flop 104. This causes the flip flop to emit a steady signal on its Q output, which is used to activate a failure-to-sense indicator 106.

The pulse from the AND gate 102 also causes the $\overline{Q}$ output of the flip flop 104 to make a negative transition which in turn is sensed by the NAND gate 58 of FIG. 3 to produce the command signal for slowing the playback tape speed. The "clear" input of the flip flop 104 receives a reset pulse L at the beginning of each rapid scanning sequence from the one-shot 72 of FIG. 4.

Figure 6:
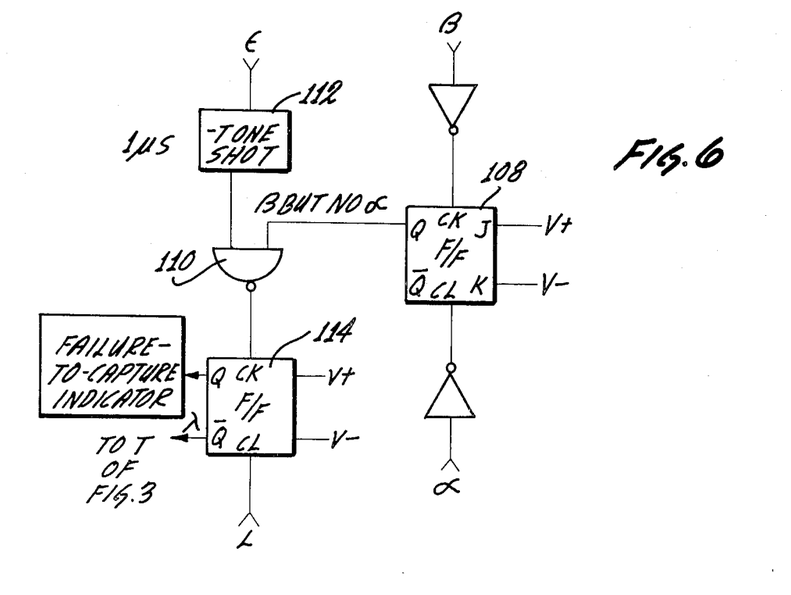
FIG. 6 is a circuit diagram of the failure-to-capture circuit.

Turning now to the failure-to-capture circuit of FIG. 6, the flip flop 108 is clocked by the beta signal indicating the occurrence of a pacemaker spike. The flip flop 108 is cleared by the alpha signal indicating the beginning of a QRS complex. Thus, the Q output of the flip flop 108 persists as long as the pacemaker spike is not followed by a QRS complex. Whether this condition has persisted for 40 milliseconds of real time is determined by the NAND gate 110 which receives as inputs both the Q output of the flip flop 108 and a 1 microsecond pulse from the one shot 112, the latter being triggered by the negative-going trailing edge of the epsilon pulse marking the end of a 40 millisecond (real time) interval following the pacemaker spike. The output pulse of the NAND gate 110 is used to clock the flip flop 114. The Q and $\overline{Q}$ outputs of the flip flop 114 are used to activate a failure-to-capture indicator and to reduce the playback speed in a manner similar to that discussed in connection with flip flop 104 of FIG. 5.

Figure 7:
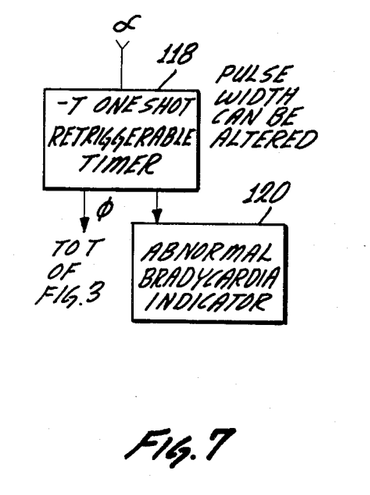
FIG. 7 is a circuit diagram of the abnormal bradycardia circuit.

As shown in FIG. 7, the abnormal bradycardia sensing circuit includes a retriggerable timer 118. No outputs are produced by the retriggerable timer 118 unless the interval between successive alpha pulses exceeds a pre-set, alterable amount of time. The retriggerable timer 118 in a preferred embodiment is a retriggerable one-shot having a positive-going output and a negative-going output. It is retriggered by alpha pulses and the positive-going output remains high so long as the pre-set time constant is not exceeded. When a pause longer than the pre-set value occurs, the negative-going output of the timer 118 goes high, turning on the abnormal bradycardia indicator 120. The positive-going output is applied to one of the inputs of the triple NAND gate 58 of FIG. 3 to generate a command signal for reducing the playback speed.

The foregoing detailed description is illustrative of a preferred embodiment of the invention, and it is to be understood that additional embodiments thereof will be obvious to those skilled in the art. The embodiments described herein together with those additional embodiments, are considered to be within the scope of the invention.

What is claimed is:

1. In a magnetic tape recorder for recording signals indicative of the operation of a pacemaker and of the response of a patient to the pacemaker as revealed by the time relationship between a pacemaker spike signal generated by the pacemaker and an ECG generated by the patient equipped with the pacemaker, said magnetic tape recorder having at least two channels for recording separate tracks on a magnetic tape, each channel including a pre-emphasis filter, at least a pair of ECG electrodes to be connected to the patient for receiving said pacemaker spike signal and said ECG signal;

first means for sensing the occurrence of a pacemaker spike signal, said pacemaker spike signal having a frequency spectrum higher than the frequency spectrum required to pass the ECG signal, and for producing in response to the pacemaker spike signal a synthesized signal whose frequency spectrum lies within the frequency spectrum required to pass the ECG signal; and second means for separating and recording the synthesized signal and the ECG signal through respective ones of said channels on separate tracks on magnetic tape, whereby the synthesized signal is recorded by a recorder normally used for recording ECG signals.

2. The apparatus of claim 1 wherein said first means further comprise:

a differentiator circuit connected to the ECG electrodes to receive as an input signal the signals educed by the ECG electrodes, and responsive to the input signal to produce a differentiator output signal related to the rate of change of the input signal;

a synthesized signal generator connected to said differentiator circuit to receive the differentiator output signal and to generate said synthesized signal when the magnitude of said differentiator output signal exceeds a preset threshold level, said synthesized signal having a predetermined waveform capable of passing through the pre-emphasis filter of the recorder so as to be recorded.

3. The apparatus of claim 2 wherein said synthesized signal is a pulse of duration longer than 10 milliseconds.

4. The apparatus of claim 3 wherein said synthesized signal generator is a one-shot multivibrator.

5. The apparatus of claim 2 wherein said synthesized signal has an amplitude greater than 0.5 millivolt.

* * * * *